United States Patent
Bonnal

[11] Patent Number: 6,146,352
[45] Date of Patent: Nov. 14, 2000

[54] IMPLANTABLE DRAINAGE VALVE FOR THE TREATMENT OF HYDROCEPHALUS

[75] Inventor: Olivier Bonnal, Cagnes sur Mer, France

[73] Assignee: Cordis SA, Viry Chatillon, France

[21] Appl. No.: 08/822,513

[22] Filed: Mar. 24, 1997

[30] Foreign Application Priority Data

Mar. 26, 1996 [FR] France .................................. 96 03721

[51] Int. Cl.[7] ...................................................... A61M 5/00
[52] U.S. Cl. .................................. 604/8; 604/9; 604/247
[58] Field of Search ...................... 604/8–10, 246–249, 604/335; 600/29–31; 137/529, 530, 539

[56] References Cited

U.S. PATENT DOCUMENTS 3,674,050  7/1972  Kuffer et al. .
3,889,687  6/1975  Harris et al. .
5,368,556  11/1994  Lecuyer .

FOREIGN PATENT DOCUMENTS 2143008  1/1985  European Pat. Off. .

Primary Examiner—Corrine McDermott
Assistant Examiner—David J. Cho
Attorney, Agent, or Firm—Dennison, Meserole, Scheiner & Schultz

[57] ABSTRACT

An implantable drainage valve for the treatment of hydrocephalus includes a housing having an opening at each end and a fluid passageway therebetween, a valve seat within the housing at one end, a closure element dimensioned to be seated in the valve seat, a spring member within the housing secured at the opening opposite the valve seat and a feeder disposed between the closure element and the spring which transmits force from the spring to the closure member. When the housing is in a substantially vertical position, the closure is subjected to a downward force including a force from the spring and the weight of the feeder.

7 Claims, 1 Drawing Sheet

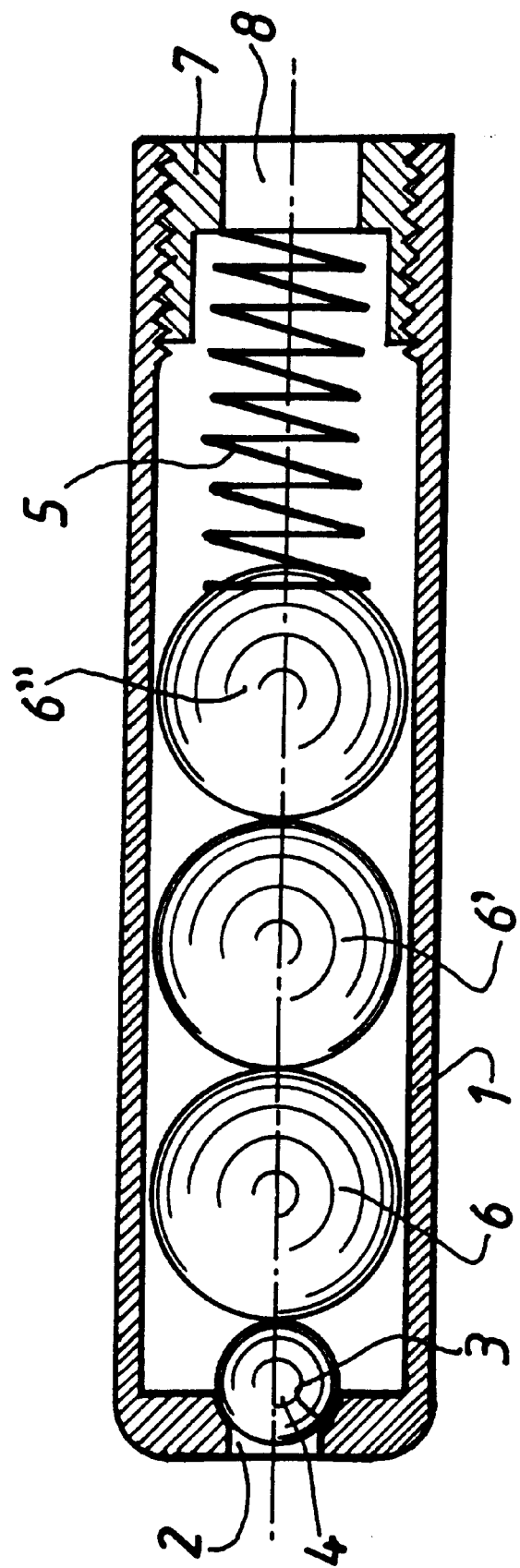

IMPLANTABLE DRAINAGE VALVE FOR THE TREATMENT OF HYDROCEPHALUS

BACKGROUND OF THE INVENTION

The present invention relates to an implantable drainage valve for the treatment of hydrocephalus, and more particularly to such a valve of the type comprising a body forming a valve seat, a closing element, a spring arranged so as to press the closing element onto the seat, and a feeder compensating for differences in the height of the liquid column depending on the position of the patient carrying the valve.

There are already known various kinds of valves designed to control the drainage of excess cerebrospinal fluid from inside the cerebral ventricles into, for example, the peritoneal cavity.

Thus document EP-A-0617975 describes such a valve comprising a body forming a valve seat, a closing element such as a ball, and a spring, one end of which presses the closing element onto the body, ie. a flap-type valve. In this document, the valve also comprises a feeder on which bears the opposite end of the spring to the closing organ.

With such a valve it is possible to take into account differences in the height of the liquid column depending on the position, notably sitting or lying down, of the patient. For when the valve is in a horizontal position, the ball is only subjected to the upstream/downstream differential pressure and to the force exerted by the spring. In the vertical position, however, the feeder, whose weight is greater than the force of the spring, slightly compresses the latter, and its weight acts in place of the force of the spring, pushing the ball onto its seat, consequently with a greater force.

Although this valve is generally speaking satisfactory, it presents the drawback that in a vertical position, the feeder can move around to a certain extent within its housing. There may result undesirable dynamic or ballistic effects during jerky movement such as running, dynamic effects which may jeopardize the satisfactory functioning of the device.

SUMMARY OF THE INVENTION

The present invention is designed to overcome these drawbacks.

To this end, the object of the invention is an implantable drainage valve for the treatment of hydrocephalus, comprising a body forming a valve seat, a closing element, a spring arranged so as to press the closing element onto the seat, and a feeder compensating for differences in the height of the liquid column depending on the position of the patient in whom the valve has been implanted, characterized in that the said feeder is disposed between the said closing element and one end of the spring, the other end of which is bearing on an abutment element.

Consequently, the spring acts on the closing element via the feeder. The valve is implanted in the patient so that, when he or she is lying down, the feeder is unsupported by the closing element and only the force of the spring is exerted on the closing element. However, when the patient is in an upright position, the closing element supports the feeder whose weight is added to the force of the spring, thus compensating for the height of the liquid column corresponding to the upright position.

In one particular embodiment of the invention, the said other end of the spring is bearing on an element firmly attached to the body or else, naturally, on the body itself.

BRIEF DESCRIPTION OF THE DRAWINGS

A description will now be offered, on a non-limiting exemplary basis, of a particular embodiment of the invention, with reference to the one appended FIGURE showing an axial sectional view of a valve according to the invention.

DESCRIPTION OF THE PREFERRED EMBODIMENTS

This valve comprises a tubular cylindrical body 1 open at both ends. The periphery of the upstream opening 2 forms a conical seat 3 onto which a closing ball 4 is pressed by a helical spring 5 via three balls 6, 6' and 6" forming a feeder.

The feeder ball 6 is pressed onto the closing ball 2, the ball 6' onto the ball 6, and the ball 6" onto the ball 6'. One end of the spring is bearing on the ball 6" and its other end is bearing on an annular screw 7, maintaining all the above components within the tubular body 1 and forming in its centre the downstream opening 8 of the valve.

During use, the upstream opening 2 is connected to a catheter, the unattached end of which is placed in the cerebral ventricle to be drained, and the downstream opening 8 is connected to a drainage catheter, the unattached end of which is brought into the peritoneal cavity.

The valve is implanted in the patient such that, when he or she is in an upright position, its axis is substantially vertical. The ball 2 is then subjected to a vertical downward force, which presses it onto the seat 3, equal to the sum of the force exerted by the spring plus the weight of the balls 6, 6' and 6".

However, when the patient is lying down, the balls 6, 6' and 6" are supported by the inner wall of the body 1, such that the ball 2 is only subjected to the force of the spring.

What is claimed is:

1. An implantable drainage valve for the treatment of hydrocephalus, comprising:
    a housing having a first fluid opening a one end thereof, a second fluid opening at an opposite end thereof and a fluid passageway therebetween;
    a valve seat within said passageway at said first fluid opening;
    a closure element dimensioned to be seated within said valve seat;
    a spring member within said housing having a first end and a second end, said first end being secured at said second fluid opening; and
    a feeder disposed between said closure element and the second end of said spring member which transmits force from the spring to the closure member,
    wherein when said housing is in a substantially vertical position, the closure member is subjected to a downward force including a force from the spring and weight of the feeder.

2. A valve according to claim 1, wherein the first end of the spring bears on an abutment element firmly attached to the housing.

3. A valve according to claim 2, wherein the abutment element is attached to the housing by screw threads at the opening at the opposite end.

4. A valve according to claim 1, wherein the closure member is a ball dimensioned to fit into said valve seat.

5. A valve according to claim 1, wherein said feeder comprises at least one ball.

6. A valve according to claim 1, wherein said feeder comprises a plurality of balls arranged in series between the closure member and the second end of the spring.

7. A valve according to claim 1, wherein the housing is generally cylindrical in shape.

* * * * *